United States Patent
Tom et al.

[11] Patent Number: 5,977,687
[45] Date of Patent: Nov. 2, 1999

[54] PIEZOELECTRIC END POINT SENSOR FOR DETECTION OF BREAKTHROUGH OF FLUID, AND FLUID PROCESSING APPARATUS COMPRISING SAME

[75] Inventors: Glenn M. Tom, New Milford; Cynthia A. Miller, Bethel, both of Conn.

[73] Assignee: Advanced Technology Materials, Inc., Danbury, Conn.

[21] Appl. No.: 08/678,572

[22] Filed: Jul. 12, 1996

[51] Int. Cl.[6] .................................................. H01L 41/08
[52] U.S. Cl. .................... 310/316.01; 310/311; 310/312; 310/321; 73/23.2; 73/31.03; 73/24.03
[58] Field of Search ................................ 310/312, 313 R, 310/340, 373 R, 313 C, 321, 311, 316, 317, 318, 319, 323, 324, 328

[56] References Cited

U.S. PATENT DOCUMENTS

| | | | |
|---|---|---|---|
| 4,056,803 | 11/1977 | White et al. | 340/15 |
| 4,446,720 | 5/1984 | Sinclair | 73/23 |
| 4,637,987 | 1/1987 | Minten et al. | 436/151 |
| 4,735,081 | 4/1988 | Luoma et al. | 73/23 |
| 5,037,624 | 8/1991 | Tom et al. | 423/210 |
| 5,138,869 | 8/1992 | Tom | 73/31.03 |
| 5,151,110 | 9/1992 | Bein et al. | 55/75 |
| 5,151,395 | 9/1992 | Tom | 502/67 |
| 5,320,817 | 6/1994 | Hardwick et al. | 423/237 |
| 5,325,705 | 7/1994 | Tom | 73/31.03 |
| 5,339,675 | 8/1994 | DiLeo et al. | 73/24.04 |
| 5,385,689 | 1/1995 | Tom et al. | 252/194 |
| 5,417,821 | 5/1995 | Pyke | 204/153 |
| 5,445,008 | 8/1995 | Wachter et al. | 73/24.06 |
| 5,476,002 | 12/1995 | Bowers et al. | 73/24.01 |
| 5,573,728 | 11/1996 | Loesch et al. | 422/90 |
| 5,705,399 | 1/1998 | Larue | 436/501 |

Primary Examiner—Mark O. Budd
Attorney, Agent, or Firm—Steven J. Hultquist; Oliver A. M. Zitzmann

[57] ABSTRACT

A sensor for detection of a trace fluid component in a fluid environment, comprising: a piezoelectric crystal having a fundamental resonant frequency in response to an applied oscillating electric field; a coating on the piezoelectric crystal of a sensor material which is reactive with the trace fluid component to yield a solid interaction product of changed mass in relation to initial mass of the sensor material interacting with the trace fluid component to yield the solid interaction product; means for applying an oscillating electric field to the piezoelectric crystal which generates an output resonant frequency therefrom; means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment; and means for flowing fluid from the fluid environment to the coating on the piezoelectric crystal so that the trace fluid component when present reacts with the coating to form the solid interaction product; wherein the coated piezoelectric crystal exhibits a frequency response rate to the trace fluid component in the range of from about 0.001 to about 1000 Hertz/min/(part-per-million of the fluid component). The sensor may be utilized for sensing of breakthrough in dry scrubbing of gases in semiconductor manufacturing, as well as for sensing of contaminant and hazardous gas species in ambient fluid environments, for environmental monitoring applications.

15 Claims, 6 Drawing Sheets

PIEZOELECTRIC END POINT SENSOR FOR DETECTION OF BREAKTHROUGH OF FLUID, AND FLUID PROCESSING APPARATUS COMPRISING SAME

BACKGROUND OF THE INVENTION

1. Field of the Invention

The present invention relates to a sensor for detection and monitoring of low/trace concentration fluid components, to a fluid processing apparatus and method utilizing same. The sensor apparatus and method of the invention have utility, inter alia, as an end point detector for the semiconductor manufacturing industry.

2. Description of the Related Art

In the conventional use of dry scrubbers, i.e., sorbent beds that reactively remove undesired components of gas streams flowed therethrough, it is critically important that the approach of the bed to exhaustion of its removal capacity thereof be accurately determinable. If the exhaustion of the removal capability of the bed is not detected by operating personnel, then gas requiring treatment will pass untreated through the bed and be passed to discharge, disposal or other process steps, still containing the components desired to be removed from such treatment effluent.

Such non-treatment, or inadequate treatment as the point of exhaustion is approached, may entail severe consequences. By way of example, dry scrubbers are used extensively in the semiconductor manufacturing industry, where the scrubber is employed to abate hazardous gases from the effluent from the processing plant, or specific operating components thereof. The failure to detect exhaustion of the scrubber bed thus may result in deleterious exposure of facility personnel to hazardous gases, as well as environmental contamination in the ambient surroundings of the semiconductor process facility. Additionally, incidents have been reported in which eductor devices downstream of scrubbers have experienced plugging when impurities have broken through the scrubbers without being detected.

Accordingly, it has been common practice either to require change-out of the scrubber bed, viz., replacement of the scrubber material in the bed with fresh scrubber medium, well prior to the actual exhaustion of the scrubber bed, i.e., with a substantial safety margin in respect of the operating life of the scrubber bed, or else to deploy monitors that detect actual or incipient breakthrough of the scrubbable components in the gas stream egressing the scrubber bed.

The first alternative, of change-out of the scrubber material well in advance of the exhaustion of the capacity of the scrubber bed, although effective in terms of preventing discharge of scrubbable components in the effluent gas, is inefficient in respect of the wastage of scrubber medium which could otherwise be employed to remove the scrubbable component, so that the effective capacity of the scrubber bed is not utilized. As a result, the scrubber bed must be oversized to accommodate the unused scrubber material.

The second alternative, of using monitors that detect actual or threshold breakthrough of the scrubbable components in the scrubber beds, is expensive, and involves the use of costly devices which additionally require significant maintenance (involving replacement of consumable elements, e.g., the frequent change of color tapes in so-called MDA monitors, or frequent change of cells in monitors such as those commercially available under the trademark Enmet), require inline recalibration not infrequently, and in some instances do not to measure the impurity species properly. In general, problems of cost, accuracy and reliability plague the existing commercially available monitors in application to scrubbing systems.

Another application in which the detection of low or trace concentrations of impurities is carried out is the monitoring of air or other ambient gases for the presence of trace hazardous gases. The systems currently commercially available such as the aforementioned MDA monitors or Kitagawa tubes, are either costly or else do not provide useful readouts. The MDA monitor is sensitive only down to concentration levels on the order of about 5 ppm, and readings below that level are inaccurate.

Accordingly it would be a significant advance in the art to provide a low cost, accurate, reliable, and easy fabricated and operated sensor device for monitoring of impurity species in fluid environments, such as gas steams discharged from a scrubber bed, or ambient gas environments which are menitored for the presence of contaminants.

It is another object of the invention to provide a highly sensitive and selective detection system for determining the presence of impurity species in fluid environments.

It is a further object of the invention to provide an end point detector for sensing the breakthrough of impurity species in such operations as dry scrubbing of process gases.

Other objects and advantages of the invention will be more fully apparent from the ensuing disclosure and appended claims.

SUMMARY OF THE INVENTION

In one aspect, the present invention relates to a sensor for detection of a trace fluid component in a fluid environment.

Such sensor may comprise:

a piezoelectric crystal having a fundamental resonant frequency in response to an applied oscillating electric field;

a coating on the piezoelectric crystal of a sensor material which is reactive with the trace fluid component to yield a solid interaction product of changed mass in relation to initial mass of the sensor material interacting with the trace fluid component to yield the solid interaction product;

means for applying an oscillating electric field to the piezoelectric crystal which generates an output resonant frequency therefrom;

means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment; and means for flowing fluid from the fluid environment to the coating on the piezoelectric crystal so that the trace fluid component when present reacts with the coating to form the solid interaction product;

wherein the coated piezoelectric crystal exhibits a frequency response rate to the trace fluid component in the range of from about 0.001 to about 1000 Hertz/min/(part-per-million of the fluid component).

Preferably the coated piezoelectric crystal exhibits a frequency response rate to the trace fluid component in the range of from about 0.01 to about 100 Hertz/min/(part-permillion of the fluid component); more preferably, such range is from about 0.1 to about 50 Hertz/min/(part-per-million of the fluid component); and most preferably such range is from about 0.5 to about 10 Hertz/min/(part-per-million of the fluid component).

The means for flowing fluid from the fluid environment to the coating on the piezoelectric crystal may for example comprise a passage having appropriate geometry, e.g., length to diameter characteristics, and/or containing a flow limiting structure such as a frit or flow-restricting orifice, so that the flow of fluid to the coating is maintained at a level which is consistent with good sensitivity and useful sensor life.

In such sensor, the piezoelectric crystal may for example comprise a piezoelectric silica crystal. The coating of sensor material usefully may comprise a chemisorbent material which is chemically reactive with the trace fluid component. Useful piezoelectric crystals include those having a fundamental resonant frequency in the range of from about 1 megahertz to about 10 megahertz.

In the sensor of the invention, the means for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the fluid environment, and (iii) generating an output indicative of the presence of the trace fluid component in the environment, may comprise means such as a circuit including therein a cascaded array of frequency counters.

The sensor may be constructed and arranged so that the output indicative of the presence of the trace fluid component in the environment, comprises a calculated concentration of said trace fluid component in said environment.

In one embodiment of the invention, the sensor further comprises a flow control means for controllably flowing a selected flow rate of fluid from the fluid environment into contact with the sensor material on the piezoelectric crystal, and the aforementioned means for performing functions (i), (ii) and (iii), comprise computational means for determining the calculated concentration of the trace fluid component in the fluid environment, in accordance with the algorithm:

$$dF/dt = \delta \cdot [C_i] \cdot Q$$

wherein:

dF/dt is the time-variant differential rate of change of frequency from the fundamental resonant frequency of the piezoelectric crystal coated with the sensor material as sampled by the means for performing functions (i), (ii) and (iii);

$\delta$ is a proportionality constant;

$[C_i]$ is the concentration of the trace fluid component; and

Q is the volumetric flow rate of the fluid of the fluid environment.

The sensor in another embodiment further comprises a flow passage accommodating flow therethrough of fluid of the fluid environment, and having a diffusional flow restrictor in the passage, arranged in relation to the sensor material to permit substantially only diffusional flow from the flow passage through the diffusional flow restrictor to the sensor material. Such diffusional flow restrictor additionally is constructed and arranged to prevent particulate solids in the fluid environment from contacting the sensor material.

The sensor may further comprise means for removing substantially all sensor material-interactive components other than the selected trace fluid component from the fluid, before the fluid contacts the sensor material. Such removing means may advantageously comprise a chemisorbent medium having sorptive affinity for sensor material-interactive components other than the selected trace fluid component.

The sensor material in one aspect may comprise a thin film metal, such as copper, zinc, silver, aluminum, chromium, or the like.

In another aspect, the invention relates to a fluid scrubbing assembly for processing of impurity-containing fluid, comprising:

a scrubber vessel containing a dry scrubber composition having sorptive affinity for impurity in the impurity-containing fluid;

means for introducing impurity-containing fluid to the scrubber vessel for contacting with the dry scrubber composition therein to remove impurity from the impurity-containing fluid, and yield treated fluid;

means for discharging treated fluid from the scrubber vessel;

a sensor for detection of impurity in the treated fluid, such sensor comprising:

(I) a piezoelectric crystal having a fundamental resonant frequency in response to an applied oscillating electric field;

(II) a coating on the piezoelectric crystal of a sensor material which is reactive with the impurity to yield a solid interaction product of changed mass in relation to mass of the sensor material interacting with the impurity to yield the solid interaction product;

(III) means for applying an oscillating electric field to the piezoelectric crystal which generates an output resonant frequency therefrom;

(IV) means for (i) sampling the output resonant frequency of the piezoelectric crystal while the oscillating electric field is applied thereto, (ii) determining the change in resonant frequency from the fundamental resonant frequency upon formation of the solid interaction product when the sensor material interacts with impurity in the treated fluid, and (iii) generating an output indicative of the presence of the impurity in the treated fluid; and means for flowing at least a portion of the treated fluid to the sensor for determining, by the output indicative of the presence of impurity, when breakthrough of impurity has occurred in the dry scrubber composition in said vessel.

A further aspect of the invention relates to a process for monitoring a fluid stream for determining presence of a selected component therein, such process comprising:

providing a sensor for detection of the selected component in the fluid stream, such sensor comprising:

(A) a piezoelectric crystal having a fundamental resonant frequency in response to an applied oscillating electric field;

(B) a coating on the piezoelectric crystal of a sensor material which is reactive with the selected component to yield a solid interaction product of changed mass in relation to initial mass of the sensor material interacting with the selected component to yield the solid interaction product;

applying an oscillating electric field to the piezoelectric crystal which generates an output resonant frequency therefrom;

sampling the output resonant frequency of the piezoelectric crystal while the oscillating electric field is applied thereto;

determining the change in resonant frequency from the fundamental resonant frequency upon formation of the solid interaction product when the sensor material interacts with the selected component in the fluid stream; and generating an output indicative of the presence of the selected component in the fluid stream.

In such process, the step of generating the output indicative of the presence of the selected component in the fluid stream, comprises determining via a programmed computer a calculated concentration of the selected component in the fluid stream.

The process may further comprise controllably flowing at least a portion of the fluid stream at a selected flow rate in contact with the sensor material on the piezoelectric crystal, and determining the calculated concentration of the selected component in the fluid stream, in accordance with the algorithm:

$$dF/dt = \delta \cdot [C_i] \cdot Q$$

wherein:

dF/dt is the time-variant differential rate of change of frequency from the fundamental resonant frequency of the piezoelectric crystal coated with the sensor material as sampled;

$\delta$ is a proportionality constant;

$[C_i]$ is the concentration of the selected component in the fluid stream; and

Q is the volumetric flow rate of the fluid stream.

In the process of the invention, the selected component may for example comprise a halide gas. By way of further example, the selected component may comprise a gas such as boron trichloride, boron trifluoride, hydrogen chloride, chlorine, fluorine, hydrogen fluoride, etc.

The process of the invention may be carried out with the sensor being constructed and arranged to be contacted by only a restricted part or portion of a main gas flow stream in a process system, so that the cumulative concentration of the impurity species reactive with the coating material on the piezoelectric crystal does not rapidly consume the coating and deplete the capacity of the sensor to detect the impurity species over a useful lifetime of operation.

In another aspect, the coated crystal is arranged in the sensor apparatus in relation to the fluid flow stream so that the coated piezoelectric crystal exhibits a frequency response rate to the trace fluid component in the range of from about 0.001 to about 1000 Hertz/min/(part-per-million of the fluid component), preferably in the range of from about 0.01 to about 100 Hertz/min/(part-per-million of the fluid component), more preferably in the range of from about 0.1 to about 50 Hertz/min/(part-per-million of the fluid component), and most preferably in the range of from about 0.5 to about 10 Hertz/min/(part-per-million of the fluid component). Such arrangement may for example entail the sampling by the coated piezoelectric crystal of a slip-stream or side-stream of a main flow of process fluid, or the restricted access of the main flow of fluid to the coated piezoelectric crystal.

In another aspect, the invention relates to a fluid scrubbing process for treating impurity-containing fluid, comprising:

contacting impurity-containing fluid with a dry scrubber composition to remove impurity from the impurity-containing fluid, and yield treated fluid;

detecting impurity in the treated fluid, by the steps comprising:
providing:

(I) a piezoelectric crystal having a fundamental resonant frequency in response to an applied oscillating electric field; and (II) a coating on the piezoelectric crystal of a sensor material which is reactive with the impurity to yield a solid interaction product of changed, e.g., increased or decreased, mass in relation to initial mass of the sensor material interacting with the impurity to yield the solid interaction product;

applying an oscillating electric field to the piezoelectric crystal which generates an output resonant frequency therefrom;

sampling the output resonant frequency of the piezoelectric crystal while the oscillating electric field is applied thereto;

determining the change in resonant frequency from the fundamental resonant frequency incident to the formation of the solid interaction product when the sensor material interacts with impurity in the treated fluid;

generating an output indicative of the presence of the impurity in the treated fluid; and flowing at least a portion of the treated fluid to the sensor for determining, by the output indicative of the presence of impurity, when breakthrough of impurity has occurred in the dry scrubber composition.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
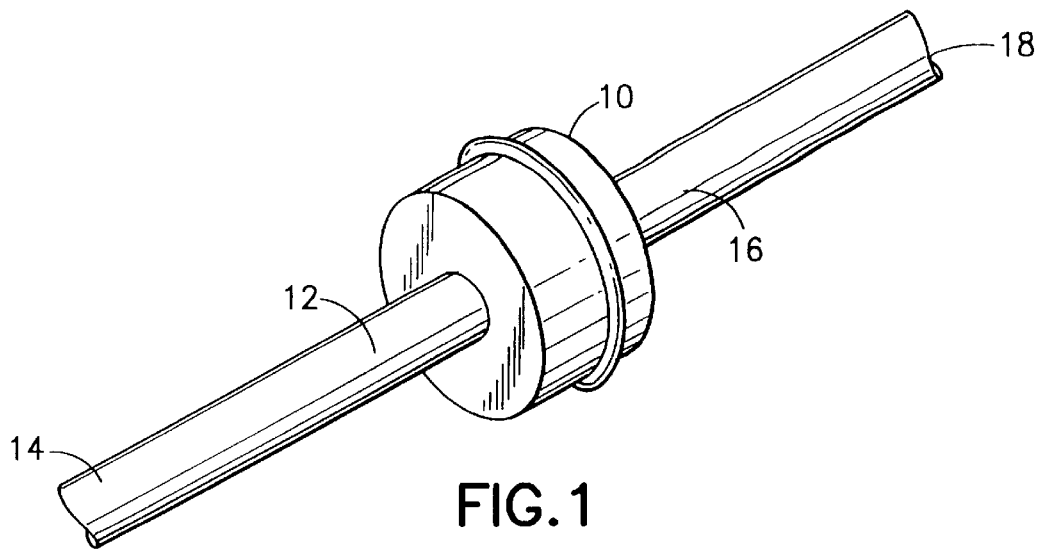
FIG. 1 is a flow restricting orifice such as may be usefully employed in the broad practice of the invention, to limit the flow of impurity-containing gas to a piezoelectric crystal sensor of the invention.

The present invention utilizes piezoelectric crystals coated with electrode sensor materials such as thin metal film coatings of Cu, Zn, Ag, Al, Cr, etc., to provide highly sensitive detectors for halide and other gases, when the gases contact and react with the electrode sensor material under operating conditions.

In the sensor of the invention, the piezoelectric crystal coated with the electrode sensor material is subjected to an input frequency, such as by means of an appropriately constructed and arranged oscillator circuit coupled in operative relationship to the piezoelectric crystal. The output frequency of the piezoelectric crystal coated with the electrode sensor material then is monitored and the change of the frequency in relation to the natural harmonic frequency of the coated crystal is determined, e.g., by a cascaded counter assembly.

By this arrangement, the contacting of a halide gas with the coating material on the crystal will cause a reaction to yield a metal halide reaction product of different mass than the initial mass of the metal on the crystal. As a result of such mass change, the frequency response characteristics of the coated crystal will change, and this frequency change thus will reflect the presence of the halide component in the gas contacted with the coating film on the piezoelectric crystal.

Accordingly, in the practice of the invention involving sensing of halide gaseous components, the frequency of an oscillator in the piezoelectric crystal circuit thus may be readily monitored to detect halogenation of the electrode, involving chemical reactions such as the following:

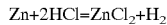
Zn+2HCl=ZnCl$_2$+H$_2$

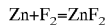
Zn+F$_2$=ZnF$_2$

It is readily feasible in the practice of the invention to tailor the reactivity of the coating material on the piezoelectric crystal, by choice of different materials, to obtain the appropriate desired sensitivity to different trace gases. For example, set out below are several illustrative thermodynamic equilibrium constants, for the reaction of HCl with different electrode (piezoelectric crystal coating) materials:

2HCl(g)+2Ag=2AgCl+H$_2$(g) Keq=10$^6$

2HCl(g)+2Cu=CuCl+H$_2$(g) Keq=10$^{17}$

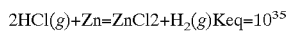
2HCl(g)+Zn=ZnCl2+H$_2$(g) Keq=10$^{35}$

From this list one would predict that of these three piezoelectric crystal coating materials, Zn would be the most sensitive to HCl, and Ag would be the least. In like manner, a desired sensitivity coating material can readily be selected, for various other and specific gas components of interest, in a given sensing or monitoring application of the present invention.

In the broad scope of practice of the present invention, the piezoelectric crystal features a coating of a material which is interactive with the gas species of interest, to yield an interaction product which alters the frequency response of the piezoelectric crystal, so that the presence of the gas species is readily detectable in the gas contacted with the coated crystal.

Thus, the coating material may suitably comprise a material which is irreversibly chemically reactive with the gas species of interest, to produce a reaction product which is of a different mass than the original coating material, being either greater or smaller in magnitude in relation to the virgin coating on the crystal.

In the use of coating materials which are consumed in contact of the gas species of interest therewith, the sensor coating can be consumed in scrubbing applications by breakthrough of impurities from the scrubber bed, so that the concentration of the impurities is suddenly increased from a zero or near-zero concentration to a high concentration. The coating can also be consumed in such scrubbing applications by a continuing low level leakage in the scrubber system. If the lifetime of the scrubber bed is sufficiently long, the sensor could be used up before the breakthrough of the scrubber bed occurs. An end point sensor product, therefore, needs to be designed to alert the user if there is a "gas alarm" condition indicative of breakthrough of the gas species from the scrubber bed, or a "system fault" condition indicative of a continuing leak of the gas species of interest which has consumed a significant portion of the coating material. The sensor system may therefore be constructed and arranged so that a gas alarm is tripped if a sufficient rate of change of the frequency over time has occurred. The sensor system may also be constructed and arranged so that system fault will occur if the life of the coated crystal has been terminated, or if the capacity of the sensor coating has been substantially exhausted before a sufficiently large rise in frequency has been obtained.

This gas alarm and system fault distinction can be accommodated by measuring the differential frequency rate of change, dF/dt (F=frequency), and the change in frequency from the start of the life of the sensor. If a large dF/dt is measured, such measurement indicates the occurrence of breakthrough of impurity from the scrubber bed. If no large dF/dt is measured but the sensor response has damped out from weight gain (of reaction product incident to leakage impurity reacting with the coating material slowly over a period of time), such response damping indicates that the sensor has been consumed without impurity breakthrough of the scrubber bed.

This use of two "trip points," indicative of impurity breakthrough as well as significant leakage consumption of the coating material, is unique in the design and operation of scrubber systems, and achieves a substantial advance in the art.

As an illustrative embodiment of the invention, the frequency response curve of a sensor system for sensing of chloride gases with a zinc electrode coating on the piezoelectric coating can be described using the equation below. This equation contains a chloride gas concentration term, a gas flow rate term, and water, pressure and temperature terms (the water term reflecting the presence of relative humidity moisture in the gas being sensed). Lifetime of the piezoelectric crystal is not included in this equation because for the breakthrough or endpoint sensor used for scrubbing applications, coating lifetime can be treated as linear and is therefore taken into account with a numerical constant, α, as a coefficient in the equation. In other applications such as environunental monitor sensors, the sensor coating lifetime will be reflected as a separate term in the algorithm. The equation for the scrubber breakthrough sensor is:

$$dF/dt = \alpha[\text{HCl}][\text{Flow Rate}][7.3-7.4*10^{-(0.00056)[H_2O]}]bdP/dt + gdT/dt + \text{noise terms}$$

wherein:
F=frequency (Hz);
α=general coefficient for chloride gas concentration, flow rate and water concentration;
b=pressure coefficient which is small relative to the first term in the equation; and
g=temperature coefficient which is small relative to the first term in the equation.

For the use of the sensor in scrubber applications, the water concentration variable, the pressure and the temperature noise terms are added to the constant, α. To avoid complications a new constant for the simplified equation will be represented as k. The simplified equation for the end point application then becomes:

$$dF/dt = k[\text{HCl}][\text{Flow Rate}]$$

wherein:
k=proportionality constant which includes the water concentration, temperature coefficient, pressure coefficient and lifetime terms.

With a zinc coated sensor, k≈40 Hz(min)$^{-1}$(ppm)$^{-1}$ (lpm)$^{-1}$ at a water concentration of about 2500 ppm. This sensitivity is sufficiently high so that breakthrough of impurity in the scrubber bed can be detected within a few minutes of breakthrough transition first occurring. Due to the first order dependence on flow in the above equation, it is important to have a constant known flow through the sensor housing in which the sensor element comprising the coated piezoelectric crystal is disposed for contacting with the gas egressing the scrubber bed.

Another issue which is important in the scrubber bed applications of the invention is keeping particulates away from the sensor element, in order to avoid false alarms due to additional loading of the particulates on the crystal.

To maintain such a constant flow and to avoid contamination of the sensor element with particulates, a frit or a flow restrictor may be deployed in the gas flow passage, e.g, conduit, through which the gas being sampled is flowed. Such flow restriction means may be employed to force the flow to be purely or substantially diffusional in character, and it will act as a particle filter at the same time. An example of such a flow restrictor device 10 is shown in FIG. 1, interposed between conduit 12, whose end 14 is joined to the sensor housing (not shown) and conduit 16, whose end 18 is joined to the manifold of the scrubber bed assembly (also not shown).

The flow restrictor may in a specific embodiment comprise a ¼" teflon plug in a KF25 tee which has a single ⁵⁄₁₆"–18 tapped hole in it to allow diffusion of the gas to the sensor. The single hole will provide enough medium for gas to diffuse through without clogging.

If there are many particulates in the gas stream then in place of such a single hole flow restrictor, a porous frit may alternatively be utilized.

In some instances, the gas being monitored for the presence of a specific halide may contain other halide species, or more generally, the coating material used in the sensor may be chemically reactive with a number of species in the gas. In such instances, it may be necessary to provide ancillary treatment of the gas to remove the species thereof which are not of interest in the monitoring or detection process.

For example, if the sensor is not selective for chloride gas of a specific type, but rather responds similarly to all three chloride gases in a gas containing $BCl_3$, HCl and $Cl_2$ which is undergoing scrubbing treatment, then it may be desirable to install a guard column or other extraneous chloride gas removal means, upstream of the sensor receiving the gas being monitored.

Thus, a reactive chemical removal agent for use in a guard column can be selected by examination of standard electrode potentials. For example, in the case of a two-component gas mixture (HCl and $Cl_2$) where the sensor is intended to selectively detect HCl but not $Cl_2$, electrode potential analysis shows that Fe(II) may be usefully employed in a guard column to obtain this selectivity. A positive net electrode potential (E°) yields a favorable reaction, and a negative E° yields an unfavorable reaction, in respect of the following reactions:

$$Fe(II) + Cl_2 \rightarrow Fe(III) + 2Cl^- \quad E° = 0.589 \text{ V (favorable)}$$

$$FeCl_2 + HCl \rightarrow FeCl_3 + \tfrac{1}{2}H_2 \quad E° = -0.771 \text{ V (unfavorable)}$$

Cu or Cu(I) would also be sufficient for this purpose, as shown by the following reactions:

$$Cu + Cl_2 \rightarrow Cu(I) + 2Cl^- \quad E° = 0.84 \text{ V (favorable)}$$

$$Cu(I) + Cl_2 \rightarrow Cu(II) + 2Cl^- \quad E° = 1.207 \text{ V (favorable)}$$

$$Cu + HCl \rightarrow CuCl_2 + H_2 \quad E° = -0.52 \text{ V (unfavorable)}$$

$$CuCl + HCl \rightarrow CuCl_2 + H_2 \quad E° = -0.153 \text{ V (unfavorable)}$$

Pb or Ca would not be suitable candidate materials for such purpose because they both react favorably with HCl and $Cl_2$.

To determine the proper species of removal agent for the guard column one must examine the standard electrode potentials of the components. If the addition of the electrode potentials for the two components is positive then the reaction is favorable, and if the addition is negative then the reaction will not occur readily. There are many possible choices for materials which will selectively react with the gas component to be "masked" from exposur e to the sensor. Care must be exercised in this determination to pick a reactive component which reacts only with the gas species to be masked, and not the gas species to be sensed by the piezoelectric sensor.

Modification of the sensor coatings to provide oxidizing characteristics may be utilized as a suitable technique to provide sensitivity to hydride gases. For example, oxidation of a Cu, Cr, or Ag electrode coating to the corresponding oxide salt may be carried out for such purpose. Such oxides react with the hydrides to form non-volatile salts (and hydrogen/water). There is a net gain in weight (relative to the starting sensor coating material) when such reaction occurs. Mass-sensitive piezoelectric sensors can thus be used to readily and economically detect the occurrence of such reaction:

$$3CuO + 2AsH_3 \rightarrow Cu_3As_2 + 3H_2O$$

As in the case of the chloride reactions, it is possible within the broad scope of the invention to readily tailor the reactivity of the sensor material and guard bed reactive material for a specific end use application of the present invention.

As described, the sensor device of the present invention may be readily fabricated and deployed to provide accurate and reliable sensing of impurity species of interest in gas scrubbing applications of the type wherein a solid scavenger or chemisorbent material having removal capability for the impurity is contacted with the gas to remove the impurity therefrom, and wherein the sensor is utilized to determine the presence of breakthrough and/or leakage of the impurity from the bed or beds in the scrubbing system.

The gas sensor of the present invention also has utility for environmental monitoring applications in which the coated piezoelectric crystal is provided to sense the presence of undesired components in a fluid environment such as air or other ambient gases.

Figure 2:
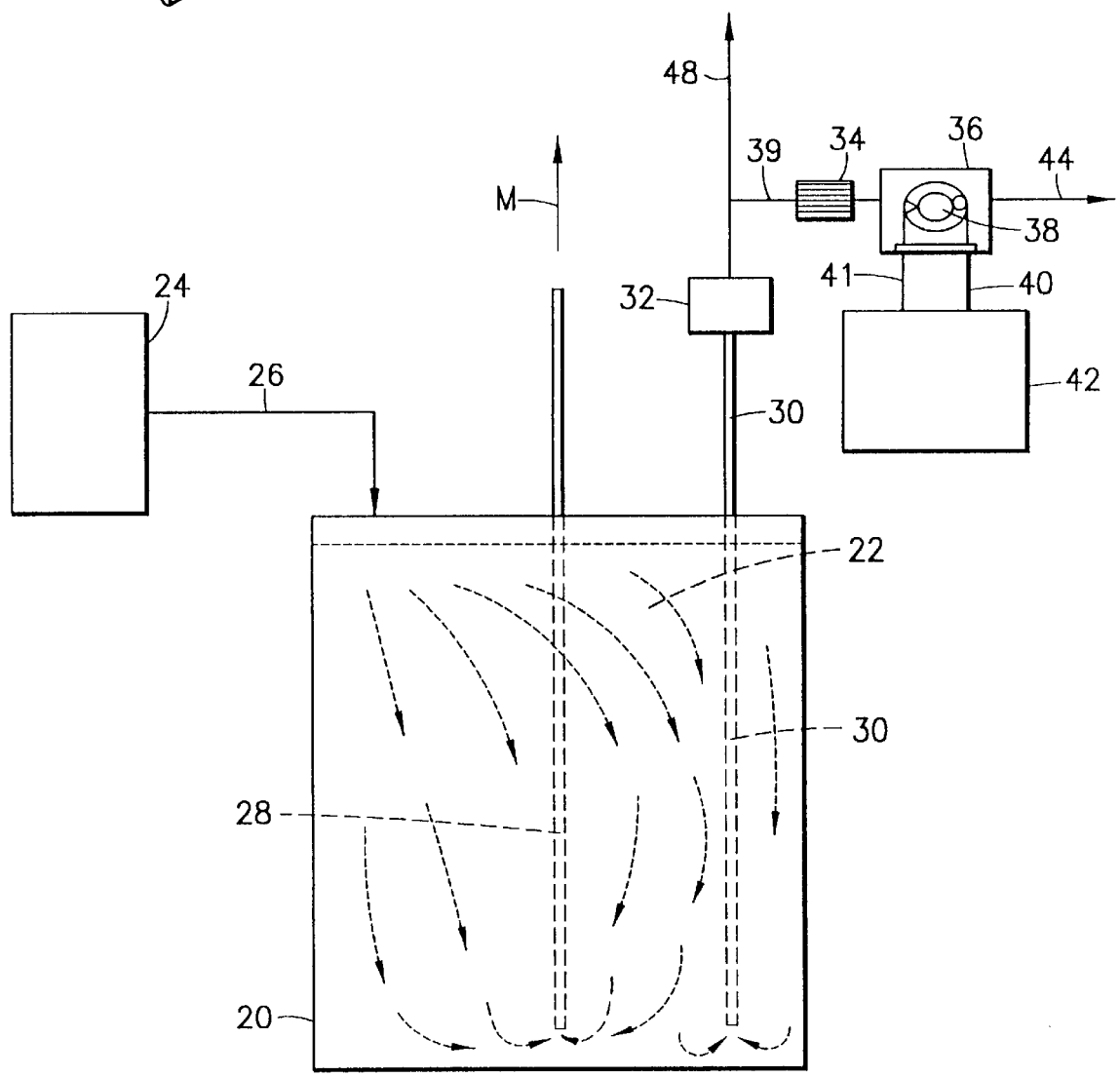
FIG. 2 is a schematic view of a dry scrubber system featuring a piezoelectric crystal sensor assembly according to one embodiment of the invention.

FIG. 2 is a schematic view of a dry scrubber system featuring a piezoelectric crystal sensor assembly according to one embodiment of the invention. This process system comprises a scrubber vessel 20 containing a quantity of a dry scrubber material 22 as a bed or mass in the vessel. The dry scrubber vessel 20 is arranged in receiving relationship to the process facility 24, which discharges a waste gas in line 26. The waste gas stream containing the impurity to be scrubbed from the gas enters the dry scrubber vessel in line 26 for scrubbing therein to deplete the gas of scrubbed component.

The dry scrubber vessel 20 has a vertically upstanding discharge conduit 28 disposed in the interior volume of the scrubber vessel, with its lower end open to receive scrubbed gas for flow upward in the conduit 28 and discharge therefrom at the open upper end of the conduit in the direction indicated by arrow M. The open upper end of the conduit 28 terminating exteriorly of the scrubber vessel 20 may be arranged to discharge the scrubbed gas to an exhaust means of the process facility, or otherwise such conduit at its open upper end may be joined to other flow passage means or apparatus for further treatment and/or disposition of the scrubbed gas.

The dry scrubber vessel 20 also has disposed therein and terminating exteriorly thereof a sampling conduit 30 receiving scrubbed gas at its open lower end for flow upwardly therein. Exterior of the scrubber vessel 20, a guard bed 32 is provided in conduit 30 for removing from the scrubbed gas stream any extraneous impurities which may react with the reactive coating of the piezoelectric sensor 36, and thereby adversely affect the sensor's accuracy for the impurity species of interest.

The guard bed may therefore contain a chemisorbent scavenger for the extraneous impurity species, so that the sample gas stream in conduit 39 is passed to the piezoelectric sensor depleted in such extraneous fluid component(s). Intermediate the guard bed 32 and the piezoelectric sensor 36 is an optional flow restriction, which may for example be of the type illustratively shown in FIG. 1, for the purpose of maintaining the flow rate of the sample gas passed to the piezoelectric sensor at a level consistent with good operating life characteristics of the sensor.

As an alternative flow restricting feature, the diameter of the conduit 30 may be significantly less than the diameter of conduit 28, so that the side stream in conduit 30 is correspondingly only a portion of the flow discharged from the vessel 20 in conduit 28.

As a still further alternative flow restricting feature, the conduit 30 may with the conduit 48 downstream of the guard bed 32, form a main flow passage for discharge of scrubbed gas from the scrubber vessel (in lieu of, or in addition to, the conduit 28), and the conduit 39 may be provided with appropriate dimensions to attenuate the flow of gas to the piezoelectric sensor 36. For example, the conduit 39 may have a diameter which is smaller than the diameter of conduits 30 and 48, or alternatively, the conduit 39 may simply by virtue of its length from the junction with conduit 48 to the sensor 36 serve to diminish the flux of the sampled scrubbed gas to an appropriate level.

Thus, the main flow of scrubbed gas from the scrubber vessel may be substantial, e.g., 40 liters per minute or more, and such gas flow would if directly contacted with the sensor coating rapidly deplete the coating even at low trace levels of the impurity, due to the cumulative large volume which would be experienced by the coating.

Accordingly, it is desired in the practice of the present invention to restrict the flux of the sampled gas stream to the sensor such that the coated piezoelectric crystal exhibits a frequency response rate to the trace fluid component in the range of from about 0.001 to about 1000 Hertz/min/(part-per-million of the fluid component), preferably in the range of from about 0.01 to about 100 Hertz/min/(part-per-million of the fluid component), more preferably in the range of from about 0.1 to about 50 Hertz/min/(part-per-million of the fluid component), and most preferably in the range of from about 0.5 to about 10 Hertz/min/(part-per-million of the fluid component). Such arrangement may as previously described entail the sampling by the coated piezoelectric crystal of a slip-stream or side-stream of a main flow of process fluid, or the restricted access of the main flow of fluid to the coated piezoelectric crystal.

The sampled gas stream after contact with the coating on the piezoelectric sensor is discharged from the sensor 36 in line 44, from which the sampled gas may be recycled to the main gas stream, or otherwise disposed of in the process facility.

As shown in FIG. 2, the piezoelectric sensor 36 comprising coated crystal 38 is operatively coupled, e.g., by signal transmission lines 40 and 41 to electronics module 42.

The electronics module includes suitable output means, e.g., comprising a liquid crystal display (not shown), which may numerically display a concentration value or other information for the impurity gas being monitored. Alternatively, the output means may provide a calorimetric display, e.g., with red indicating a hazardous or dangerously high concentration of the gas component of interest, yellow indicating a tolerable but high concentration of the gas component, and green indicating that the gas component concentration is within acceptable concentration limits. As still other alternatives, the output means may comprise a audible alarm, other visual display (e.g., a flashing light), or any other suitable output means.

The electronics module 42 is constructed and arranged for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with the trace fluid component in the sampled fluid stream, and (iii) generating an output indicative of the presence of the trace fluid component in the fluid stream, with the coated piezoelectric crystal exhibiting a frequency response rate to the trace fluid component in the range of from about 0.001 to about 1000 Hertz/min/(part-per-million of the fluid component).

Figure 3:
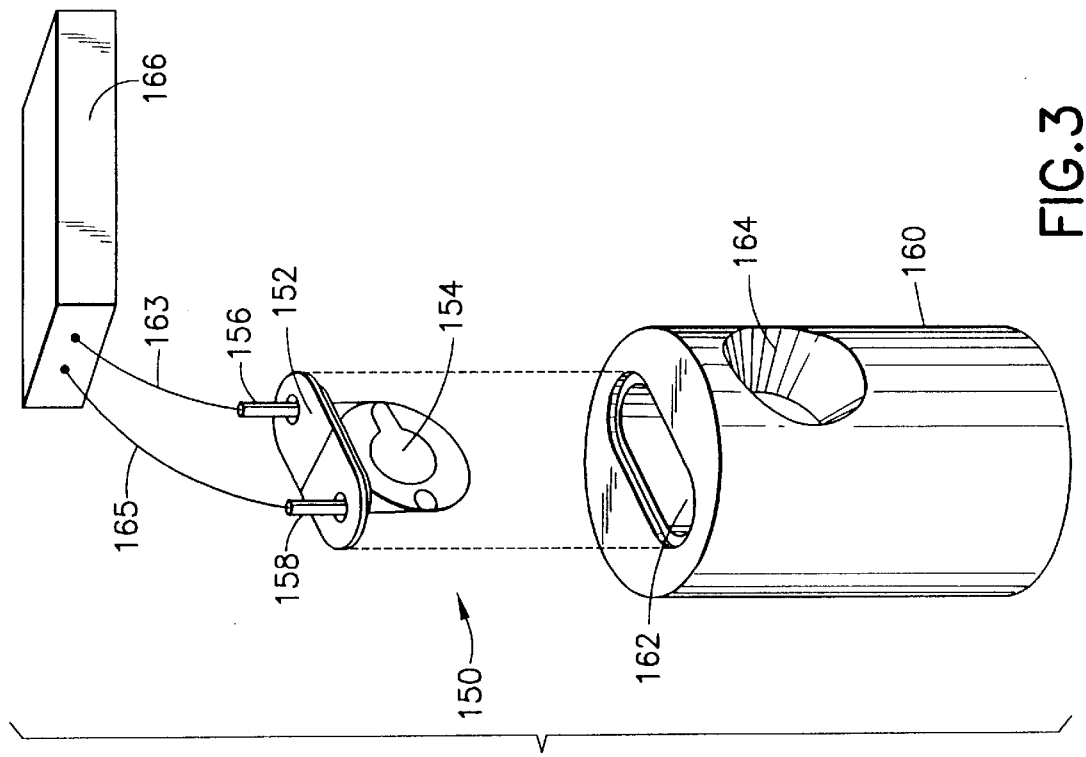
FIG. 3 is a sensor assembly for a scrubber system, according to another embodiment of the invention.

FIG. 3 shows an exploded view of a sensor assembly according to another embodiment of the invention, comprising the sensor element 150 and the housing 160. The sensor element 150 comprises the piezoelectric crystal 154 which is coated with a suitable material interacting with the fluid component of interest to yield an interaction product of differing mass characteristic than the original coating material. The coated crystal is mounted on the plug member 152, with the respective leads of the piezoelectric crystal 154 protruding exteriorly of the plug member when the plug member is engaged with the housing 160 with the coated crystal extending into the cavity 162.

The housing 160 features an opening 164 by which a gas can be flowed into the cavity 162 containing the sensor element 150. Although not shown in the front perspective view of FIG. 3, the housing 160 has another opening therein, opposite opening 164 and in register with such opening, for discharge from the housing of the gas flowed past the coated piezoelectric crystal.

The leads 156 and 158 of the sensor element may be coupled in circuit relationship to suitable electronics means shown schematically as electronics module 166 in FIG. 3, by which the presence and concentration of the gas impurity species can be detected. The electronics module 166 is coupled to the sensor element leads 156 and 158 by wires 163 and 165, respectively.

Electronics module 166 provides the functions of (i) sampling the output resonant frequency of the piezoelectric crystal while the oscillating electric field is applied thereto, (ii) determining the change in resonant frequency from the fundamental resonant frequency incident to the formation of the solid interaction product when the sensor material interacts with the trace fluid component in the fluid being monitored, and (iii) generating an output indicative of the presence of the trace fluid component in such fluid.

In a specific embodiment of the sensor assembly shown in FIG. 3, the housing 160 may comprise an aluminum housing which has the cavity 162 machined into it for insertion of the sensor element, as well as two feedthrough (¼" NPT) openings (opening 162 and the opposite opening not shown in FIG. 3) for the gas to flow through the sensor. In the body of this housing is the flow restricting orifice. This ¼" aluminum housing fits directly on the scrubber vessel and the front end driver electronics are plugged directly onto the legs (leads 156 and 158) of the sensor assembly. The resulting assembly may be coupled to a sensor tube of the scrubber vessel, or otherwise joined in flow sensing communication with the scrubber vessel or scrubber bed therein.

Figure 4:
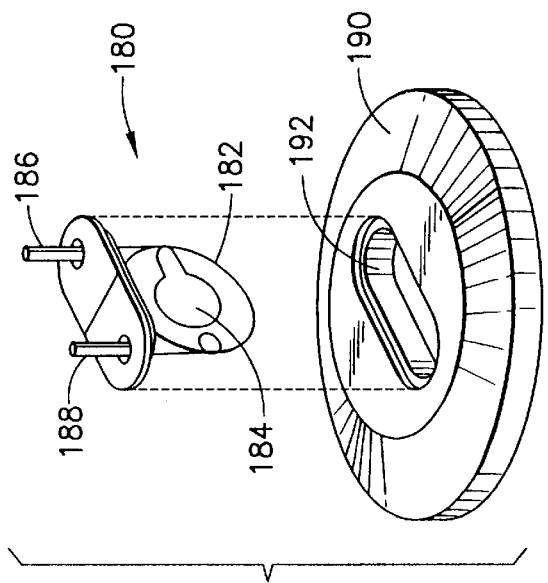
FIG. 4 is a sensor assembly for a scrubber system, according to still another embodiment of the invention.

FIG. 4 is an exploded perspective view of another sensor assembly according to the present invention, comprising the sensor element 180 and the receiving fitting 190. The sensor element 180 comprises the piezoelectric crystal 182 which is coated with a suitable material interacting with the fluid component of interest to yield an interaction product of differing mass characteristic than the original coating material. The coated crystal is mounted on the plug member 184, with the respective leads 186 and 188 of the piezoelectric crystal protruding exteriorly of the plug member when the plug member is engaged with the receiving fitting 190 with the coated crystal extending into the cavity 192.

In a specific embodiment, the receiving fitting comprises a KF25 blank which will fit into a KF25 tee having a flow restricting orifice in the same leg as the sensor. The electronics associated with the sensor element plug directly into the legs of the sensor unit (leads 186 and 188).

It will be appreciated that the sensor device of the invention may assume a wide variety of conformations and arrangements in the broad practice of the invention, consistent with the specific end use of the sensor device, and the nature and extent of the output function thereof.

Figure 5:
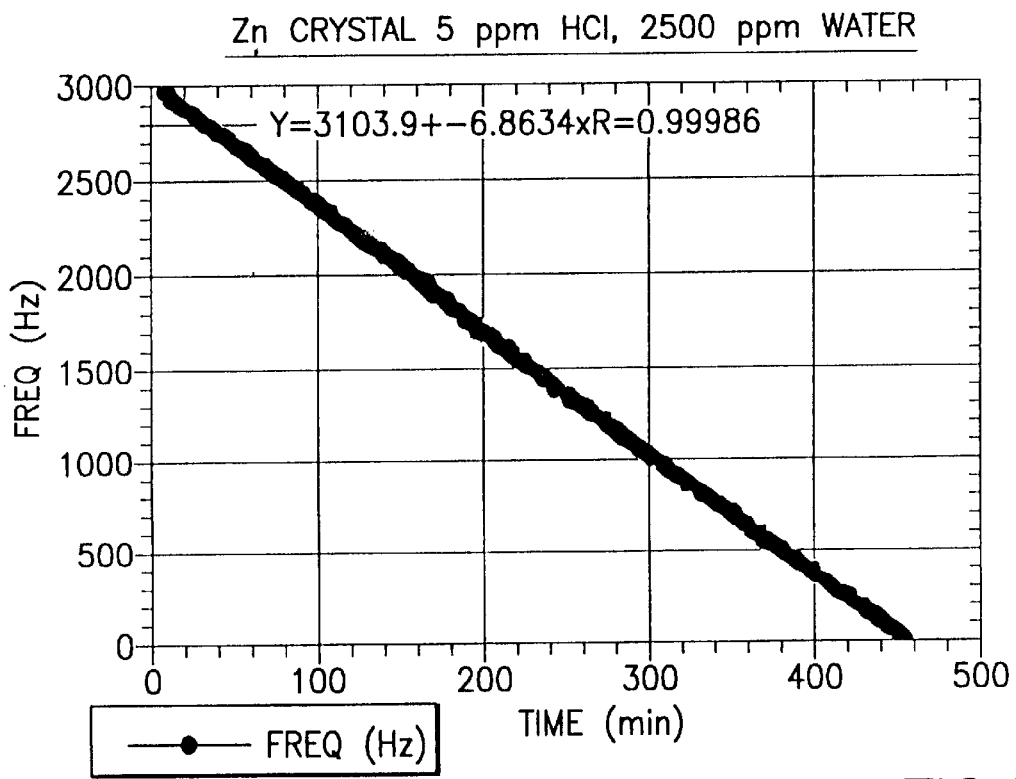
FIG. 5 is a graph of frequency response as a function of time, for a Zn electrode piezoelectric crystal sensor, in exposure to HCl at 5 ppm concentration and 2500 ppm water.

FIG. 5 is a graph of frequency as a function of time, showing the frequency response of a Zn electrode piezoelectric crystal sensor according to an illustrative embodiment of the invention, in exposure to HCl. The slope of the line in this plot determines the frequency change expected over time at 5 ppm HCl, 2500 ppm HCl, and 50 sccm HCl. This number is 6.9 Hz/min. To put this number in perspective, if sampling were carried out for 10 min. the expected frequency change would be ≈70Hz, and the signal to noise (S/N) ratio is 35. Such frequency change is easily detected with the system of the present invention.

Figure 6:
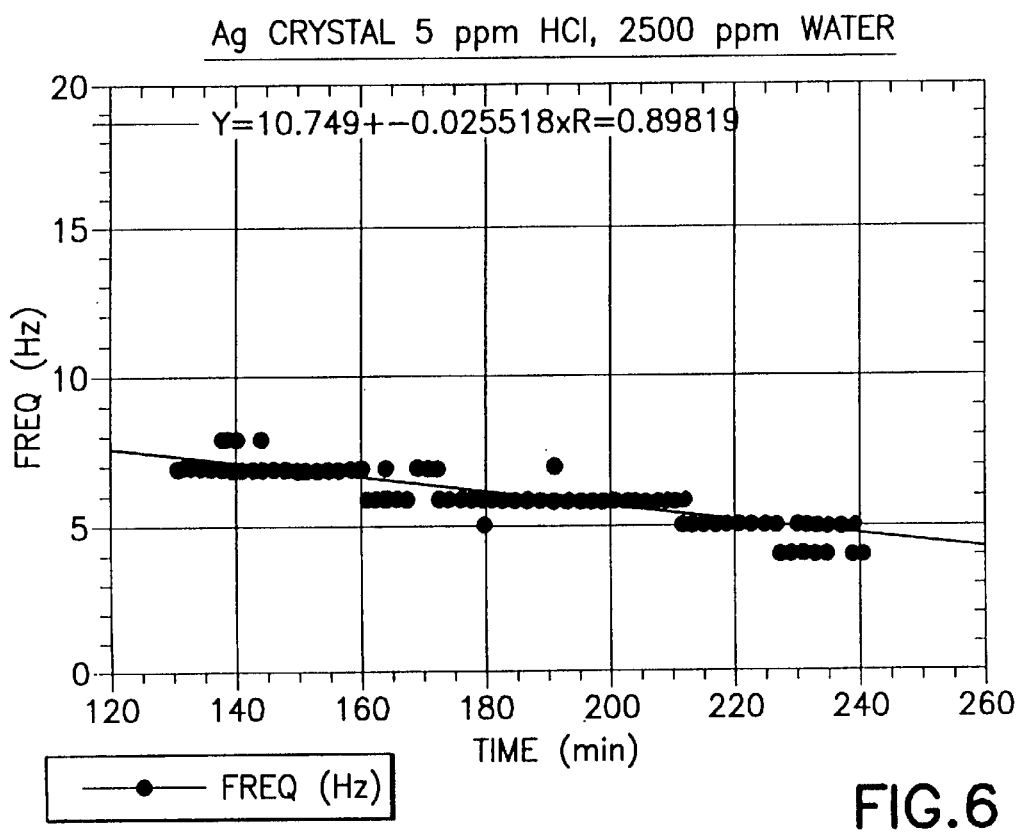
FIG. 6 is a graph of frequency response as a function of time, for a Ag piezoelectric crystal electrode sensor, in response to HCl at 5 ppm concentration and 2500 ppm water.

FIG. 6 is a graph of frequency as a function of time, showing the frequency response of a silver (Ag) electrode piezoelectric crystal sensor according to an illustrative embodiment of the invention, in exposure to HCl. The frequency response over this interval, 0.025 Hz/min, is much smaller than that obtained with the Zn electrode (see FIG. 5), and corresponds to a 0.2 Hz change at a ten minute sampling period. In general, the Ag electrode sensor is much less sensitive than the zinc electrode, as predicted hereinabove.

Figure 7:
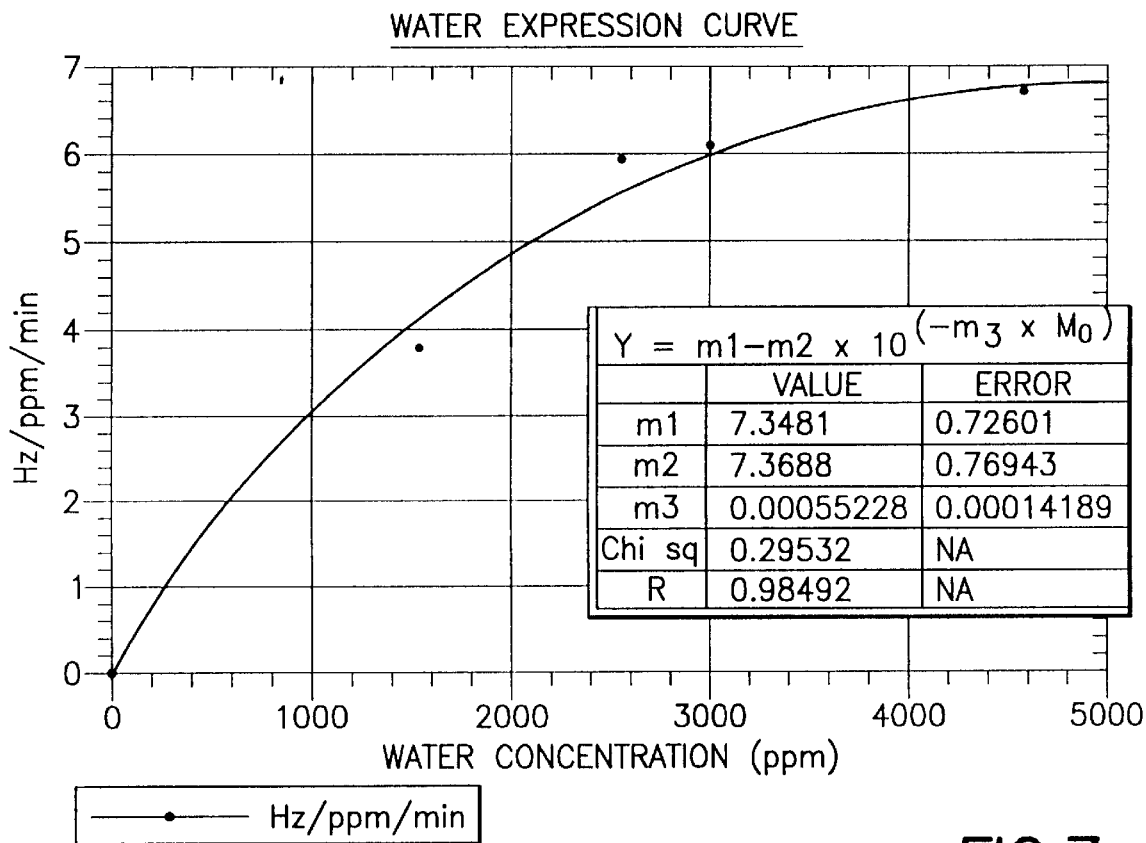
FIG. 7 is a graph of frequency as a function of water concentration, in ppm, showing the frequency response of a zinc electrode piezoelectric crystal sensor, determined with $BCl_3$.

FIG. 7 is a graph of frequency as a function of water concentration, in ppm, showing the frequency response of a zinc electrode piezoelectric crystal sensor according to an illustrative embodiment of the invention. The effect of water on the zinc sensor coating was determined by examining the frequency change over time with variation in water concentration, and with the water dependence curve determined with $BCl_3$. This figure shows that water is a catalyst in the corrosion reaction and that it accelerates the reaction to a point. At a maximum water concentration the rate of the reaction is constant. The water concentration at which the rate is constant is approximately 3000 ppm.

In relation to the previously discussed algorithm for frequency change with time, the analysis can be simplified for applications such as end point monitoring of scrubber beds (to determine breakthrough) by assuming that the water term is constant and therefore can be dropped from the equation. The pressure and temperature expressions can also be removed because they are very small relative in magnitude to the flow and chloride concentration values. In other applications where accuracy is more important these terms are retained in the equation.

Figure 8:
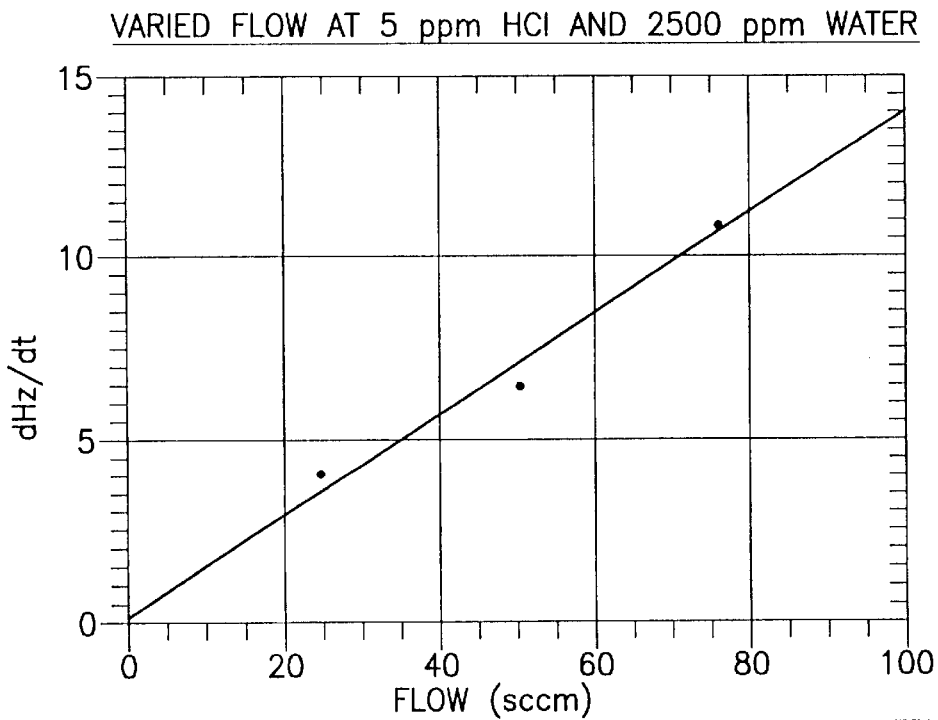
FIG. 8 is a graph showing zinc electrode coated piezoelectric crystal sensor frequency response as a function of flow in standard cubic feet of gas per minute (sccm), with varied flow at 5 ppm HCl and 2500 ppm water.

The first order flow rate dependance of the endpoint sensor of the invention in application to HCl sensing was determined by the variation of flow at constant water, temperature, pressure and HCl concentration. The resulting data are reflected in the graph of FIG. 8, showing zinc electrode coated piezoelectric crystal sensor frequency response as a function of flow in standard cubic feet of gas per minute (seem), with varied flow at 5 ppm HCl and 2500 ppm water. From this data it is seen that as the flow doubles the frequency response rate of change, dHz/dt, doubles as well, indicative of a first order dependance relationship.

Figure 9:
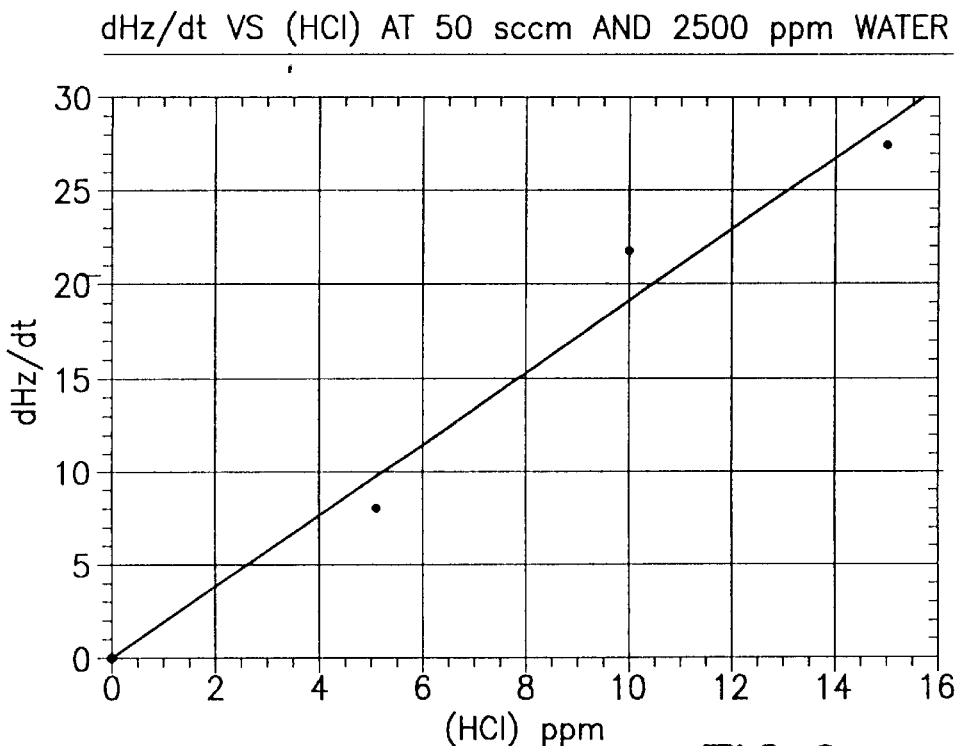
FIG. 9 is a graph of dHz/dt, the rate of frequency change, as a function of chloride concentration, for a Zn electrode sensor device, at constant flow, temperature and pressure, at 50 sccm and 2500 ppm water conditions.

FIG. 9 is a graph of dHz/dt, the rate of frequency change, as a function of chloride concentration, for a Zn electrode sensor device representative of the scrubber sensor of the present invention. FIG. 9 shows this data (dHz/dt vs HCl concentration) at constant flow, temperature and pressure, at 50 sccm at 2500 ppm water conditions.

Figure 10:
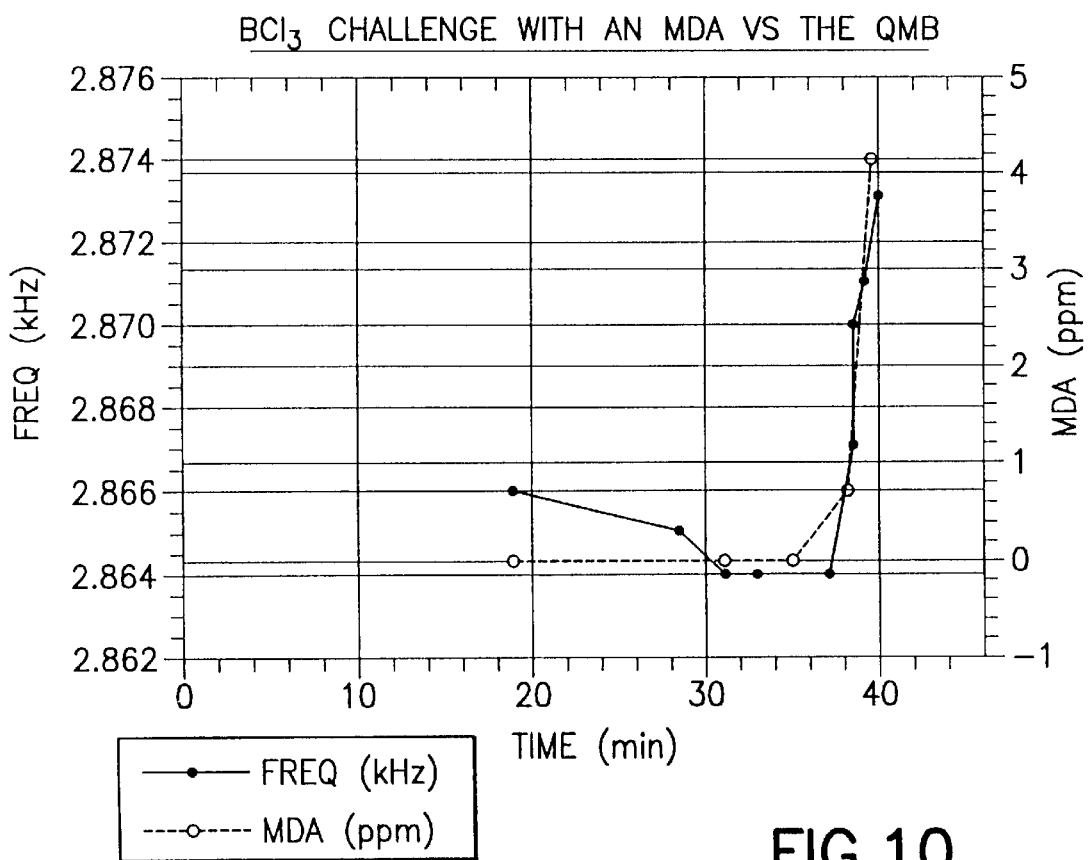
FIG. 10 is a graph of frequency as a function of time, showing the response characteristics of a sensor representative of the present invention, and the response characteristics of an MDA sensor, with boron trichloride ($BCl_3$).

FIG. 10 is a graph of frequency as a function of time, showing the response characteristics of a sensor representative of the present invention, and the response characteristics of an MDA sensor, with boron trichloride ($BCl_3$). The data show that the sensor of the present invention has similar response times as the MDA sensor.

Figure 11:
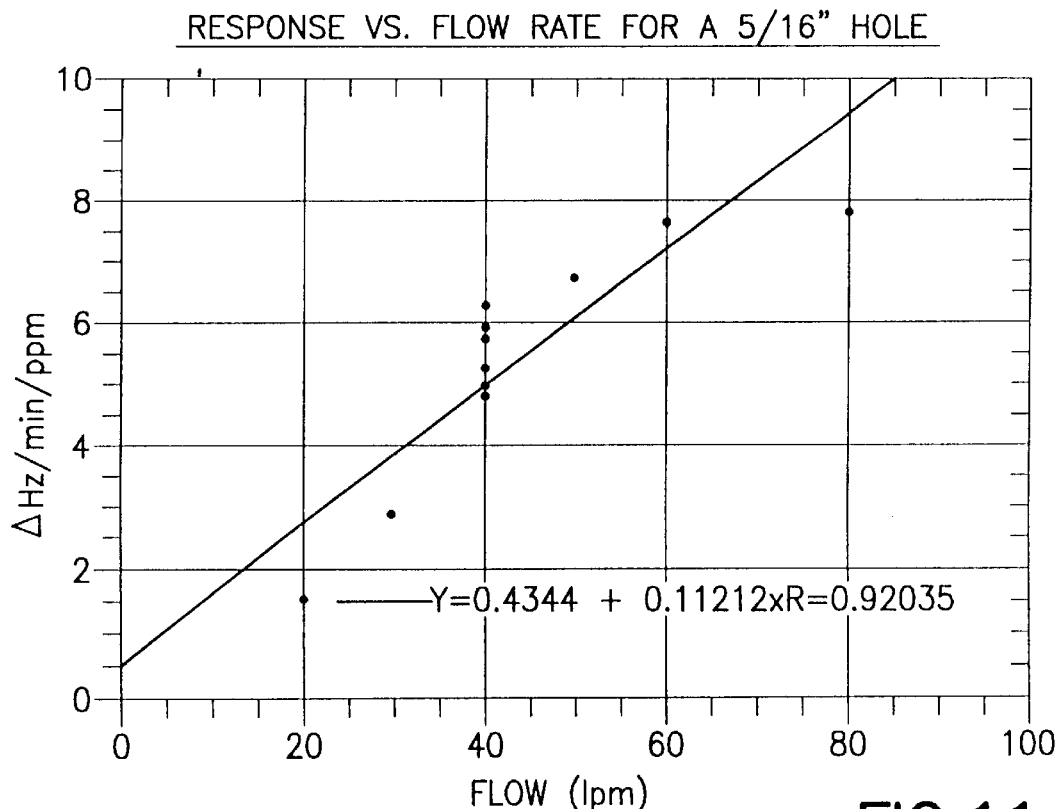
FIG. 11 is a graph of a flow rate frequency response curve for a Zn electrode piezoelectric crystal sensor utilizing a flow restricting orifice.

The response of the piezoelectric crystal sensor of the invention is proportional to the flow rate. In a high flow regime (e.g., in the range of 5 to 100 lpm) a flow restricting orifice may be present to extend the life of the crystal and to control its response. FIG. 11 is a graph of the frequency response (change of frequency per unit time per ppm of HCl), as a function of flow rate of gas in liters per minute (lpm). This graph shows the frequency response of a Zn electrode piezoelectric crystal sensor to HCl at different flow rates when utilizing a flow restricting orifice with an inside diameter of 5/16 inch.

Figure 12:
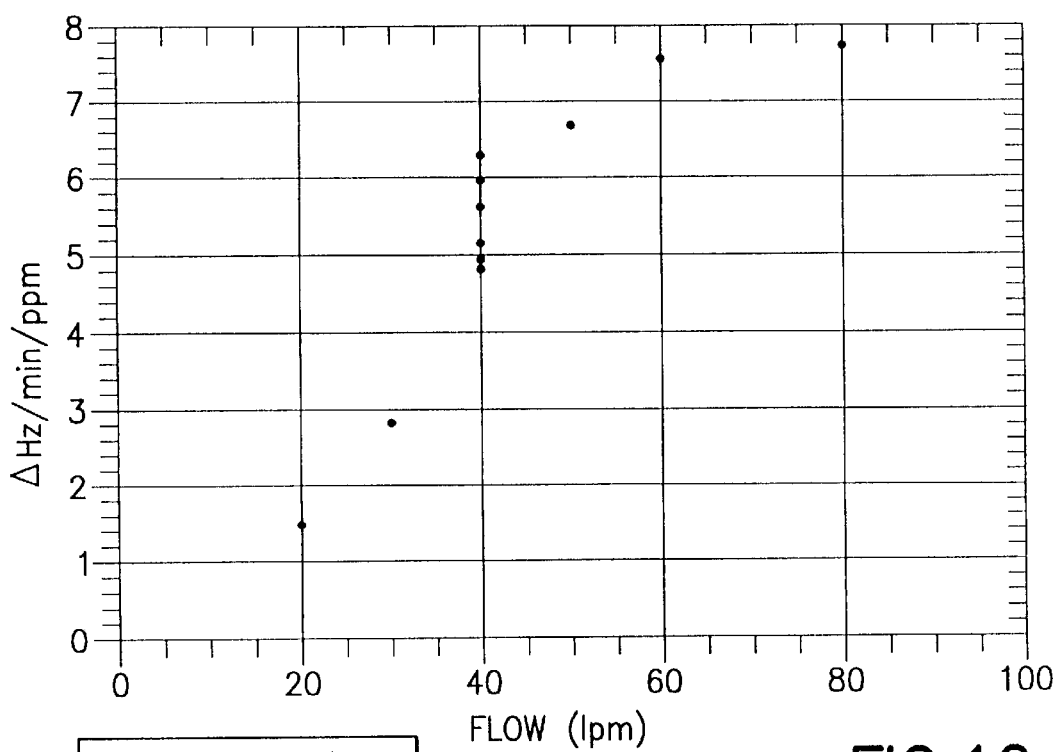
FIG. 12 is a graph of the rate of change of frequency per unit of trace impurity, as a function of the flow rate of the fluid stream containing such impurity, for a Zn electrode piezoelectric sensor according to one embodiment of the invention, in which a 5/16 inch flow restricting orifice is employed to restrict the flow of the impurity (HCl)-containing fluid to the sensor.

FIG. 12 is a graph of the rate of change of frequency per unit of trace impurity, as a function of the flow rate of the fluid stream containing such impurity, for a Zn electrode piezoelectric sensor according to one embodiment of the invention, in which a 5/16 inch flow restricting orifice is employed to restrict the flow of the impurity (HCl)-containing fluid to the sensor. As shown by this graph, the flow restriction afforded by the orifice is sufficient to accommodate a 40 liter per minute flow of HCl-containing gas, restricting the flux at the Zn coating on the piezoelectric crystal so that the frequency/minute/ppm of HCl is in the range of 4.8 to 6.4, thereby providing excellent dynamic frequency response characteristics consistent with superior operating life of the sensor.

The foregoing data and examples show that the piezoelectric crystal sensor of the invention provides an effective and simple means and method for determining the presence of a dilute or trace component in a gas. The invention contemplates the provision on a piezoelectric crystal substrate of a reactive coating which posesses high sensitivity and selectivity for a wide variety of gas species, e.g., chlorides, fluorides, hydrides, etc.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A single piezoelectric crystal sensor assembly for detecting a trace gaseous component in a gaseous environment, comprising:
   a. a coated piezoelectric crystal sensor for emitting a resonant frequency, said sensor comprising:
      a piezoelectric crystal having a fundamental resonant frequency in response to an applied oscillating electric field;
      a coating on the piezoelectric crystal comprising a sensor material which undergoes an irreversible chemical reaction with the trace gaseous component to yield a solid reaction product of changed mass in relation to the initial mass of the sensor material;
   b. means for applying an oscillating electric field to the coated piezoelectric crystal sensor to cause the sensor to emit an output resonant frequency;
   c. means for sampling the output resonant frequency emitted by the coated piezoelectric crystal sensor;
   d. means for determining the rate of change of the output resonant frequency during formation of the solid reaction product;
   e. means for generating an output indicative of the presence of the trace gaseous component in the gaseous environment; and
   f. means for flowing fluid from the gaseous environment to the coated piezoelectric crystal sensor so that the trace gaseous component when present reacts with the coating to form the solid reaction product;

wherein said means (d) and (e) comprise computational means for determining said calculated concentration of said trace fluid component in the fluid environment, in accordance with the algorithm:

$$dF/dt = \delta \cdot [C_i] \cdot Q$$

wherein:
dF/dt is the time-variant differential rate of change of frequency from the fundamental resonant frequency of the piezoelectric crystal coated with the sensor material;
$\delta$ is a proportionality constant;
$[C_i]$ is the concentration of the trace fluid component; and
Q is the volumetric flow rate of the fluid of the fluid environment; and wherein the coated piezoelectric crystal sensor exhibits an output resonant frequency response rate to the trace gaseous component in the range of from about 0.001 to about 1000 milliHertz/min/(part-per-million of the gaseous component).

2. A sensor assembly according to claim 1, wherein the piezoelectric crystal comprises a piezoelectric silica crystal.

3. A sensor assembly according to claim 1, wherein the coated piezoelectric crystal sensor exhibits an output resonant frequency response rate to the trace gaseous component in the range of from about 0.01 to about 100 milliHertz/min/(part-per-million of the gaseous component).

4. A sensor assembly according to claim 1, wherein the coated piezoelectric crystal sensor exhibits an output resonant frequency response rate to the trace fluid component in the range of from about 0.5 to about 10 milliHertz/min/(part-per-million of the gaseous component).

5. A sensor assembly according to claim 1, wherein the piezoelectric crystal has a fundamental resonant frequency in the range of from 1 Megaherz to 10 Megaherz.

6. A sensor assembly according to claim 1, wherein the means for (i) sampling the output resonant frequency of the coated piezoelectric crystal sensor, (ii) determining the change in resonant frequency over time from the fundamental resonant frequency that occurs on formation of the solid reaction product and (iii) generating an output indicative of the presence of the trace gaseous component in the gaseous environment, comprise a circuit including therein a cascaded array of frequency counters.

7. A sensor assembly according to claim 1, wherein said output indicative of the presence of the trace gaseous component in said gaseous environment, comprises a calculated concentration of said trace gaseous component in said environment.

8. A sensor assembly according to claim 1, further comprising a flow passage accommodating flow therethrough of gaseous of the gaseous environment, and having a diffusional flow restrictor in the passage, arranged in relation to the sensor material to permit substantially only diffusional flow from the flow passage through the diffusional flow restrictor to the coated piezoelectric crystal sensor, said diffusional flow restrictor additionally being constructed and arranged to prevent particulate solids in the gaseous environment from contacting the sensor material.

9. A sensor assembly according to claim 1, further comprising means for removing from the gaseous environment, before its contacting with the coated piezoelectric crystal sensor, substantially all coated piezoelectric crystal sensor-interactive components other than said trace gaseous component.

10. A sensor assembly according to claim 9, wherein the coated piezoelectric crystal sensor-interactive components removing means comprises a chemisorbent medium having sorptive affinity for said coated piezoelectric crystal sensor-interactive components other than said trace gaseous component.

11. A sensor assembly according to claim 1, wherein the sensor material comprises a thin film metal.

12. A sensor assembly according to claim 11, wherein the thin film metal is selected from the group consisting of copper, zinc, silver, aluminum and chromium.

13. A sensor assembly according to claim 1, wherein said means for carrying out functions b, c and d, are constructed and arranged to provide (A) an output gas alarm condition indicative of breakthrough of the trace gaseous component, and (B) an output system fault condition indicative of a continuing leak of the trace gaseous component when the trace gaseous component has consumed a significant portion of the coating material.

14. A sensor assembly according to claim 1, constructed and arranged to measure the differential frequency rate of change, dF/dt, and the change in frequency from the start of the life of the coated piezoelectric crystal sensor, whereby if a large dF/dt is measured, such measurement indicates the occurrence of breakthrough of impurity from the scrubber bed, and if no large dF/dt is measured but sensor response has damped out from weight gain incident to leakage trace impurity reacting with the coating material slowly over a period of time, such response damping indicates that the sensor material has been consumed without trace impurity breakthrough.

15. A gas scrubbing assembly for processing of impurity-containing gas, comprising:
   a. a scrubber vessel containing a dry scrubber composition having sorptive affinity for impurity in said impurity-containing gas;
   b. means for introducing impurity-containing gas to the scrubber vessel for contacting with the dry scrubber composition therein to remove impurity from the impurity-containing gas, and yield treated gas;
   c. means for discharging treated gas from the scrubber vessel;
   d. a coated piezoelectric crystal sensor for detecting impurity in the treated gas, said sensor comprising:
      (i) a piezoelectric crystal having a fundamental resonant frequency in response to an applied oscillating electric field;
      (ii) a coating on the piezoelectric crystal of a sensor material which undergoes a chemical reaction with the impurity to yield a solid reaction product of changed mass in relation to mass of the unreacted sensor material and wherein the $K_{eq}$ of the chemical reaction between the sensor material and the trace fluid component is greater than about $10^6$;
   e. means for applying an oscillating electric field to the coated piezoelectric crystal sensor to generate an output resonant frequency therefrom;
   f. means for sampling the output resonant frequency of the coated piezoelectric crystal sensor while said oscillating electric field is applied thereto;
   g. means for determining the rate of change of resonant frequency during formation of said solid reaction product; and
   h. means for generating an output indicative of the presence of the impurity in said treated gas; and
   i. means for flowing at least a portion of the treated gas to the sensor for determining, by said output indicative of the presence of impurity, when breakthrough of impurity has occurred in the dry scrubber composition in said vessel;
   wherein said means g. and h. comprise computational means for determining said calculated concentration of said impurity in said treated gas, in accordance with the algorithm:

$$dF/dt = \delta \cdot [C_i] \cdot Q$$

wherein:
   dF/dt is the time-variant differential rate of change of frequency from the fundamental resonant frequency of the piezoelectric crystal coated with the sensor material;

$\delta$ is a proportionality constant;

$[C_i]$ is the concentration of the impurity; and

Q is the volumetric flow rate of the treated gas.

* * * * *

UNITED STATES PATENT AND TRADEMARK OFFICE
CERTIFICATE OF CORRECTION

PATENT NO : 5,977,687

DATED : Nov. 2, 1999

INVENTOR(S) : Glenn M. Tom and Cynthia Miller

It is certified that error appears in the above-identified patent and that said Letters Patent are hereby corrected as shown below:

| | |
|---|---|
| Column 2, line 14: | after "Accordingly" insert --,--. |
| Column 2, line 15: | change "easy" to --easily--. |
| Column 2, line 19: | change "menitored" to --monitored--. |
| Column 9, line 4: | change "envirorunental" to --environmental--. |
| Column 9, line 48: | after "g" insert --.--. |
| Column 10, line 24: | after "2Cl" leave a space. |
| Column 10, line 31: | after "2Cl" leave a space. |
| Column 10, line 33: | after "2Cl" leave a space. |
| Column 10, line 35: | after "E°" insert --=--. |
| Column 10, line 48: | change "exposur e" to --exposure--. |
| Column 12, line 44: | change "calorimetric" to --colorimetric--. |
| Column 14, line 50: | change "(seem)" to --(sccm)--. |
| Column 14, line 57: | change "vs" to --vs.--. |
| Column 15, line 20: | change "frequency" to --Δfrequency--. |

Signed and Sealed this

Third Day of April, 2001

Attest:

NICHOLAS P. GODICI

Attesting Officer     Acting Director of the United States Patent and Trademark Office